United States Patent [19]

Izawa et al.

[11] Patent Number: 5,688,948
[45] Date of Patent: Nov. 18, 1997

[54] PROCESS FOR ISOMERIZING ACYCLIC NUCLEOSIDES AND PROCESS FOR SEPARATING PURINE NUCLEOSIDES

[75] Inventors: Kunisuke Izawa; Yoshihito Koguchi; Hiroshi Shiragami; Yumiko Uchida; Satoshi Takamatsu, all of Kawasaki, Japan

[73] Assignee: Ajinomoto Co., Inc., Tokyo, Japan

[21] Appl. No.: 454,567

[22] Filed: May 30, 1995

Related U.S. Application Data

[60] Division of Ser. No. 214,756, Mar. 18, 1994, which is a continuation-in-part of Ser. No. 917,357, Jul. 23, 1992, Pat. No. 5,336,770.

[30] Foreign Application Priority Data

Sep. 18, 1991 [JP] Japan ................... 3-238247

[51] Int. Cl.$^6$ ............... C07D 473/18; C07D 473/16; C07D 473/06; C07D 473/30
[52] U.S. Cl. ................ 544/276; 544/264; 544/265; 544/71; 544/277
[58] Field of Search ................... 544/265, 264, 544/267, 272, 276, 277

[56] References Cited

U.S. PATENT DOCUMENTS

| | | | |
|---|---|---|---|
| 4,199,574 | 4/1980 | Schaeffer | 544/276 |
| 5,336,770 | 8/1994 | Shiragami et al. | 544/276 |

OTHER PUBLICATIONS

Martin et al, J Med Chem 26, 759(1983).
Ogilvie, Can J Chem 62, 2702 (1984).
Boryski, Nucleosides & Nucleotides 6, 385(1987).
Boryski Nucleosides & Nucleotides 8, 529(1989).

*Primary Examiner*—Mark L. Berch
*Attorney, Agent, or Firm*—Oblon, Spivak, McClelland, Maier & Neustadt, P.C.

[57] ABSTRACT

Herein is disclosed a novel and industrially advantageous process for synthesizing acyclic nucleosides such as acyclovir and ganciclovir from ribonucleosides, which process comprises adding an acid catalyst and an acid anhydride to a solution of a ribonucleoside such as guanosine and an ester derivative of an acyclic sugar, and heating the mixture, whereby a transglycosilation reaction takes place between the ribose moiety of the ribonucleoside and the ester derivative of the acyclic sugar.

Herein is also disclosed an industrially favorable method for the separation of 9-substituted purine nucleosides which are important intermediates for the synthesis of acyclic nucleosides such as acyclovir, ganciclovir, and the like from ribonucleosides, which method comprises crystallizing only the 9-isomer from a solution or suspension containing both a 9-substituted purine nucleoside and a 7-substituted purine nucleoside by cooling the solution or/and by adding a crystallizing solvent thereto.

6 Claims, No Drawings

PROCESS FOR ISOMERIZING ACYCLIC NUCLEOSIDES AND PROCESS FOR SEPARATING PURINE NUCLEOSIDES

CROSS-REFERENCE TO THE RELATED APPLICATION

This is a Division, of application Ser. No. 08/214,756 filed on Mar. 18, 1994, which is a Continuation-In-Part of application Ser. No. 07/917,357, filed on Jul. 23, 1992, now U.S. Pat. No. 5,336,770.

BACKGROUND OF THE INVENTION

1. Field of the Invention

The present invention concerns a process for producing acyclic nucleosides, such as, particularly, acyclovir of the below-mentioned formula (IV) and ganciclovir of the below-mentioned formula (V), both being an anti-vital agent. Acyclovir and ganciclovir are compounds having a powerful anti-vital activity, particularly, to herpes virus both in vitro and in vivo, and have already been authorized and sold commercially as an anti-vital chemotherapeutical agent.

The present invention also relates to a method for the separation of acyclic purine nucleosides which are useful as intermediates for acyclovir and other antiviral agents.

2. Discussion of the Background

For the purpose of producing acyclovir or ganciclovir, there has been known, for example, a method of using guanine as a starting material or a method of using 2,6-dichloropurine or 2-amino-6-chloropurine. However, each of the methods has drawbacks in that the desired-compound can not be obtained in a high yield, the desired compound can not be obtained easily in a high purity, and the procedures concerned are complicated from the industrial point of view. U.S. Pat No. 4,199,574; J. R. Barrio et al., J. Med. Chem., 23, 572 (1980); and J. C. Martin et al., J. Med. Chem., 26, 759 (1983).

On the other hand, ribonucleosides such as guanosine, adenosine and inosine have been mass-produced by a fermentation process. In view of the above, it has been an important subject to develop a novel and industrially advantageous process for synthesizing acyclic nucleosides such as acyclovir and ganciclovir from the above-mentioned ribonucleosides.

With respect to the separation of purine nucleosides, the prior art is as follows.

Regarding methods for the production of acyclic purine nucleosides such as acyclovir and ganciclovir, the following are known:

a) A method which uses guanine as the starting material: U.S. Pat. No. 4,146,715.

b) A method which uses diacetylguanine as the starting material: U.S. Pat. No. 4,146,715, J. C. Martin et al., J. Med. Chem., 1983B, Vol. 26, 759, and Japanese Patent Application Laid-Open(kokai) No. 88-107982.

c) A method which uses acetylguanine as the starting material: Japanese Patent Application Laid-Open(kokai) No. 82-80685.

d) A method which uses tetraacetylguanosine as the starting material: J. Boryski et al., Nucleosides & Nucleotides, 1989, Vol. 8, 529.

e) A method which uses 2,6-dichloropurine as the starting material: U.S. Pat. No. 4,146,715.

f) A method which uses 2-chloro-6-iodopurine as the starting material: J. R. Barrio et al., J. Med. Chem. 1980, Vol. 23, 572.

g) A method which uses 2-amino-6-chloropurine as the starting material: U.S. Pat. No. 4,146,715, and K. K. Ogilvie et al., Can. J. Chem., 1982, Vol. 60, 3005.

However, all of these methods are problematic when performed on an industrial scale. According to methods a)–g), and particularly methods a)–d) which use guanine or acylated guanine derivatives, undesirable 7-isomers are produced in large amounts, which in turn necessitates in most cases non-efficient methods of separation such as silica gel chromatography in order to obtain the desired 9-isomer at a favorable degree of purity. In addition, methods e)–g) which use halogenated purines can hardly be called methods for industrial production, as their starting materials are expensive and difficult to acquire, and they demand a reaction with ammonia under conditions of high temperature and pressure in order to obtain guanine nucleosides such as acyclovir, ganciclovir, etc.

As the object acyclic nucleosides are to be used exclusively as antiviral agents or their intermediates for use in humans, it need not be mentioned that it is desirable from the point of view of safety that the amount of unnecessary isomers contained therein be as low as possible.

The present inventors have, as described hereinabove, developed a method for the production of acyclic nucleosides in order to overcome the above mentioned disadvantages, which is efficient from the point of view both of cost of starting material and of procedure, and which comprises using an inexpensive starting ribonucleoside such as guanosine, etc., reacting it with an-acylated acyclic sugar derivative, and heating the resulting mixture of a 9-isomer and a 7-isomer to isomerize the 7-isomer to the 9-isomer in the same reactor. However, even with this method, it is difficult to completely isomerize the 7-isomer, and this results in residues of the 7-isomer in the reaction mixture on the order of $1/10$ to $1/100$. Therefore, it was an urgent necessity to develop a method for the pure and highly efficient separation of the 9-isomer from a mixture of a 9-isomer and a 7-isomer.

SUMMARY OF THE INVENTION

Accordingly, an object of the present invention is to provide a novel and industrially advantageous process for synthesizing acyclic nucleosides such as acyclovir and ganciclovir from ribonucleosides mass-produced by fermentation.

In an aspect of the present invention, there is provided a process for producing an acyclic nucleoside derivative of the formula (I):

which comprises reacting a ribonucloside derivative of the formula (II):

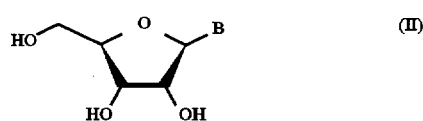

with an acid anhydride and an ester derivative of the formula (III):

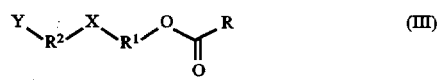

in the presence of an acid catalyst.

In another aspects of the present invention, there is provided a process for producing a nucleoside derivative of the general formula (VII):

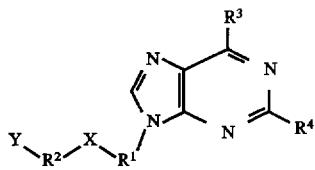

which comprises heating a purine derivative of the general formula (VI):

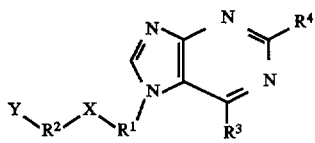

in the presence of an acid catalyst.

Another object of the present invention to provide an industrially favorable method of separation of 9-substituted purine nucleosides, which are important intermediates for the synthesis of acyclic nucleosides such as acyclovir, ganciclovir, etc. from ribonucleosides.

Other objects will become apparent from the description of the present invention given hereinbelow.

DETAILED DESCRIPTION OF THE INVENTION

With the subject in mind, the present inventors have made profound studies on the transglycosilation reactions between guanosine and a derivative of the sugar moiety of acyclic nucleosides. As a result, it has been found that a transglycosilation reaction takes place between the ribose moiety of a ribonucleoside and an ester derivative of a acyclic sugar when an appropriate acid catalyst and a carboxylic acid anhydride are added to a mixture of a ribonucleoside such as guanosine and an ester derivative of an acyclic sugar and the resultant mixture is heated. The present invention has been made on these findings.

That is, the present invention concerns a process for producing an acyclic nucleoside derivative represented by the formula (I):

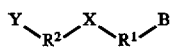

wherein B represents a purine base or pyrimidine base which may be substituted with hydroxyl group(s), amino groups(s), mercapto groups(s) and/or halogen atoms(s), each of said hydroxyl group(s), amino group(s), and mercapto group(s) being one which may be substituted with an alkyl group with 1 to 12 carbon atoms, an acyl group with 1 to 12 carbon atoms or a silyl group represented by the formula (Ia):

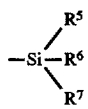

wherein $R^5$, $R^6$ and $R^7$ which may be identical with, or different from, one another represent an alkyl group with 1 to 4 carbon atoms, a phenyl group or a benzyl group, $R^1$ represents a methylene group, $R^2$ represents an alkylene group with 1 to 4 carbon atoms which may be substituted with hydroxyl group(s), amino group(s), alkoxyl group(s) with 1 to 12 carbon atoms, alkoxycarbonyl group(s), phosphono group(s), dialkoxyphosphoryl group(s), acyloxyl group(s) with 1 to 12 carbon atoms, acylamino group(s) with 1 to 12 carbon atoms, halogen atom(s) and/or silyloxyl group(s) represented by the formula (Ib):

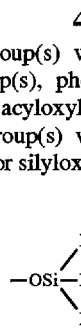

wherein $R^5$, $R^6$ and $R^7$ are the same as in the formula (Ia),

X represents an oxygen atom, a sulfur atom, or an imino group, and

Y represents a hydroxyl group, an amino group, an alkoxyl group with 1 to 12 carbon atoms, a phosphono group, a dialkoxyphosphoryl group, an alkoxycarbonyl group, an acyloxyl group with 1 to 12 carbon atoms, an acylamino group with 1 to 12 carbon atoms, a halogen atom, or a silyloxyl group represented by the above-mentioned formula (Ib), which comprises reacting a ribonucleoside derivative represented by the formula (II):

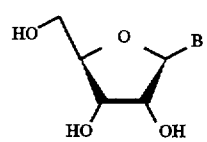

where B is the same as in the above-mentioned formula (I), in the presence of an acid catalyst, with an acid anhydride and an ester derivative represented by the formula (III):

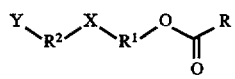

where R represents a hydrogen atom, an alkyl group with 1 to 20 carbon atoms or an aryl group with 6 to 20 carbon atoms, $R^1$ and $R^2$ are respectively the same as in the above mentioned formula (I), X and Y are respectively the same as in the above-mentioned formula (I), followed by saponification, if necessary.

The present invention also concerns a process for producing a nucleoside derivative represented by the general formula (VII):

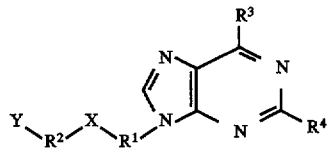

wherein $R^1$ represents a methylene group, $R^2$ represents an alkylene group with 1 to 4 carbon atoms which may be substituted with hydroxyl group(s), amino group(s), alkoxyl group(s) with 1 to 12 carbon atoms, alkoxycarbonyl group(s), phosphono group(s), dialkoxyphosphoryl group(s), acyloxyl group(s) with 1 to 12 carbon atoms, acylamino group(s) with 1 to 12 carbon atoms, halogen atom(s) and/or silyloxyl group(s) represented by the formula (Ib):

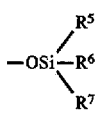 (Ib)

wherein $R^5$, $R^6$ and $R^7$ which may be identical with, or different from, one another represent an alkyl group with 1 to 4 carbon atoms, a phenyl group or a benzyl group, and $R^3$ and $R^4$ each represent independently a hydrogen atom, a halogen atom, a hydroxyl group, an amino group or a mercapto group, said hydroxyl group, amino group and mercapto group each being, if desired, substituted with an alkyl group with 1 to 12 carbon atoms, a silyl group represented by the formula (Ia), or an acyl group with 1 to 12 carbon atoms, X represents an oxygen atom, a sulfur atom, or an imino group, and Y represents a hydroxyl group, an amino group, an alkoxyl group with 1 to 12 carbon atoms, a phosphono group, a dialkoxyphosphoryl group, an alkoxycarbonyl group, an acyloxy group with 1 to 12 carbon atoms, an acylamino group with 1 to 12 carbon atoms, a halogen atom, or a silyloxyl group represented by the above-mentioned formula (Ib), which comprises heating, in the presence of an acid catalyst, a purine derivative represented by the general formula (VI):

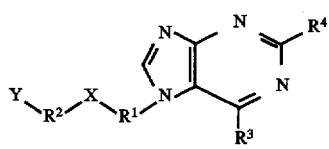 (VI)

where $R^1$, $R^2$, $R^3$, $R^4$, X and Y are respectively the same as in the above-mentioned formula (VII).

The present invention will now be described specifically illustrating a synthetic process for acyclovir of the formula (IV) and ganciclovir of the formula (V) with reference to Schemes I(a) and I(b).

Scheme I(a)

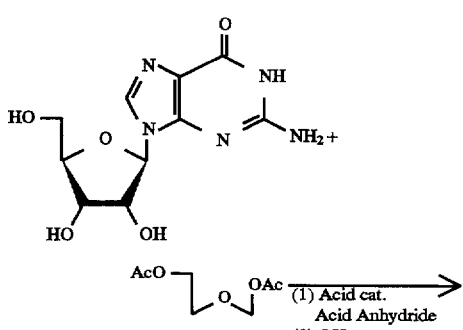

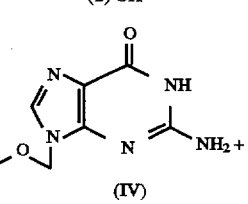
(IV)

-continued
Scheme I(a)

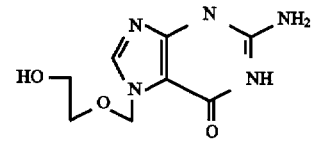

Scheme I(b)

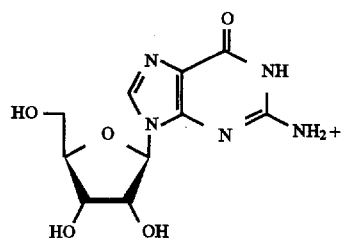

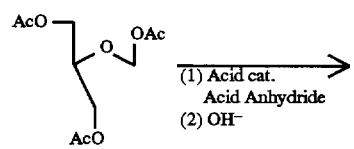

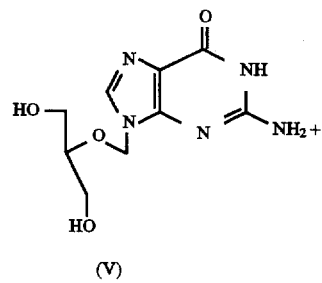

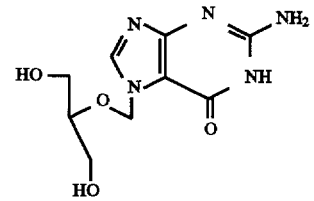
(V)

When, e.g., acetic anhydride and, e.g., p-toluenesulfonic acid monohydrate are added to a mixed solution of guanosine and 2-oxa-1,4-butanediol diacetate, and the resultant mixture is heated at, e.g., 100° C. for, e.g., 24 hours, a transglycosilation reaction takes place between the moiety of guanosine ribose and 2-oxa-1,4-butanediol diacetate. After completion of the reaction, the reaction solution is subjected to, e.g., alkaline hydrolysis, whereby acyclovir of the formula (IV) is obtained. In this transglycosilation reaction, the 7-position isomer of the acyclovir is also formed together with acyclovir. The two isomers can be separated, if necessary, from each other by, e.g., silica gel column chromatography or recrystallization.

On the other hand, when, e.g., acetic anhydride and, e.g., p-toluenesulfonic acid monohydrate are added to a mixture of guanosine and acetoxymethyl-1,3-diacetoxy2-propyl ether, the resultant mixture is heated at, e.g., 100° C. for, e.g., 24 hours, and then the reaction solution is subjected to, e.g., alkaline hydrolysis, ganciclovir of the formula (V) is obtained. Also, in this transglycosilation reaction, the 7-position isomer of ganciclovir is by-produced. The two isomers can be separated, if necessary, from each other by e.g., silica gel column chromatography or recrystallization.

According to the present invention, in what amount an ester derivative of the formula (III) should be used on the basis of a ribonucleoside of the formula (II) is not critical, and usually a ratio of 1–2:1 is chosen.

As for the acid anhydride of the present invention, an organic carboxylic acid anhydride such as acetic anhydride, propionic anhydride or benzoic anhydride or a phosphoric acid anhydride such as pyrophosphoric acid or metaphosphoric acid is used. The amount to be used is from about 1 to about 10 equivalents based on the starting material of the formula (II).

As for the acid catalyst of the present invention, acid catalysts such as organic acids, inorganic acids and Lewis acids, e.g., p-toluenesulfonic acid monohydrate, sulfanilic acid, methanesulfonic acid, trifluoroacetic acid, trifluoroboron ether complexes, sulfuric acid, phosphoric acid, and hydrochloric acid, are in general used. The catalyst is used in an amount from 1 to 20 mol % based on the starting material of the formula (II).

As for the reaction solvent, usual organic solvents such as, e.g., dimethylformamide; dimethylsulfoxide; acetonitrile; carboxylic acid such as acetic acid; carboxlic acid esters such as ethyl acetate and methyl acetate; hydrocarbons such as benzene, hexane and toluene; ethers such as diethyl ether, tetrahydrofuran and dioxane; halogenated hydrocarbons such as dichloromethane, chloroform and dichloroethane; ketones such as acetone and methyl ethyl ketone; are used. If a compound of the formula (II) is soluble in a compound of the formula (III) and an acid anhydride, the reaction of the present invention may be conducted without any solvent.

The reaction temperature is usually selected from within a temperature range of 20° to 200° C., while the reaction time is usually selected from a period of 1 hour to 1 week.

As for the ribonucleoside derivatives of the formula (II), purine nucleosides such as guanosine, adenosine and inosine, pyrimidine nucleosides such as uridine and cytidine, and the derivatives of the base moiety of such nucleoside may be used.

The acyclic sugar ester derivatives of the present invention have the structure as shown by the formula (III), having an acyl group at the terminal end. There can be mentioned, e.g., 2-oxa-1,4-butanediol diacetate as the acyclic sugar ester derivative, which can be, in turn, synthesized by reacting 1,3-dioxolane and acetic anhydride in the presence of a catalytic amount of an acid. Acyclic sugar ester derivatives thus obtained are allowed to react with ribonucleoside derivatives with or without isolation.

A desired reaction product such as acyclovir or ganciclovir can be isolated from the reaction mixture, e.g., by the treatment with an alkaline solution, followed by purification with silica gel column chromatography.

Next, the isomerization reaction will be explained.

In the transglycosilation reaction, as has already been described regarding the production of acyclovir and ganciclovir, when a purine nucleoside such as guanosine, adenosine or inosine is used as the ribonucleoside, the 7-position isomer is formed together with the 9-position isomer.

When the desired compound is a 9-position isomer such as acyclovir, isomerization of the 7-position isomer to the desired compound (a 9-position isomer) is required. The present inventors have made a study thereon, and as a result, found that the expected isomerization reaction may be realized, with the solvent distilled off or replaced with another solvent, or without isolation of the intermediate from the reaction mixture after the transglycosilation reaction by continuing the heating of the intermediate in the presence of an acid catalyst.

As shown in Scheme II, the 7-position isomer can be isomerized by heating in the presence of an acid catalyst, in the absence, or in the presence, of an appropriate solvent into the 9-position isomer such as an acyclovir derivative or a ganciclovir derivative.

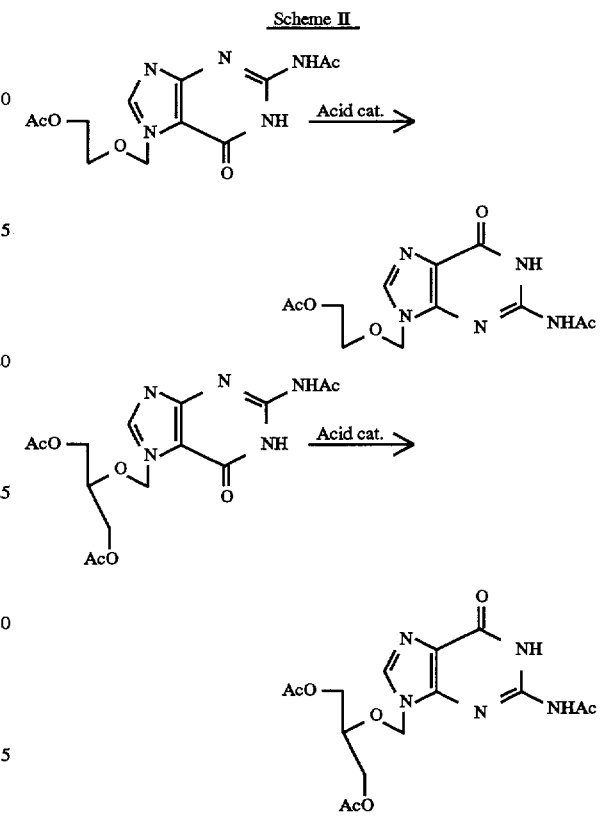

Scheme II

As for the solvent for the isomerization reaction, there can be mentioned usual organic solvents such as, e.g., carboxylic acid esters such as ethyl acetate and methyl acetate; hydrocarbons such as benzene, hexane and toluene; ethers such as diethyl ether, tetrahydrofuran and dioxane; halogenated hydrocarbons such as dichloromethane, chloroform and dichloroethane; and ketones such as acetone and methyl ethyl ketone.

The reaction is usually conducted at a temperature of 20° to 200° C., while the reaction time is usually 1 hour to 1 week.

The completion of the isomerization reaction can be confirmed by, e.g., high performance liquid chromatography. The resultant acyclovir and ganciclovir derivatives form crystals and can be isolated easily.

These derivatives give the final products, i.e., acyclovir and ganciclovir by, e.g., alkaline hydrolysis.

In order to achieve the said another object, the present inventors have conducted varied research regarding methods of separation of purine nucleosides. As a result, they have discovered that it is possible to separate 9-substituted purine nucleosides from 7-substituted purine nucleosides by crystallization, and thus the present invention has been completed on these findings.

In other words, the present invention relates to a method for the separation of the 9-substituted purine nucleoside from a solution or suspension containing a 9-substituted purine nucleoside represented by the formula (VIIa):

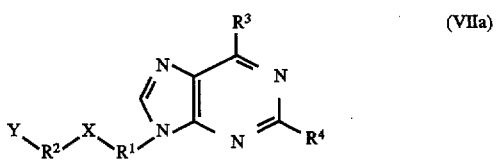

where $R^1$, $R^2$, $R^3$, $R^4$, X and Y are respectively the same as the above-mentioned formula (VII), and a 7-substituted purine nucleoside represented by the formula (VIa):

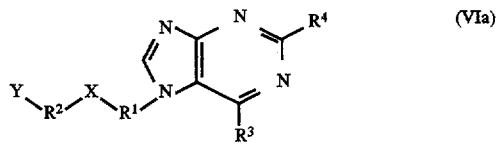

where $R^1$, $R^2$, $R^3$, $R^4$, X and Y are respectively the same as in the above-mentioned formula (VIIa), which comprises crystallizing selectively the 9-substituted purine nucleoside from said solution or suspension.

Scheme III shows some methods for the synthesis of diacetyl acyclovir, as an example, for a concrete explanation of the present invention.

formula (VIIa) and a 7-substituted purine nucleoside represented by the formula (VIa).

The crystallization is effected by either cooling a solution which contains a 9-substituted purine nucleoside and a 7-substituted purine nucleoside, or by adding a crystallizing solvent to a solution or suspension which contains a 9-substituted purine nucleoside and a 7-substituted purine nucleoside.

The cooling crystallization is effected by dissolving a mixture of a 9-substituted purine nucleoside and a 7-substituted purine nucleoside in a solvent such as water, an alcohol such as methanol, ethanol, or the like, an organic acid ester such as ethyl acetate, and the like, a hydrocarbon such as toluene, xylene, or the like, a ketone such as acetone, methyl ethyl ketone, or the like, a halogenated hydrocarbon such as chloroform, dichloromethane, or the like, an ether such as diethyl ether, tetrahydrofuran, or the like, or a nitrile such as acetonitrile, or the like, while heating if necessary, and then cooling the resultant solution. Preferably, it is effected by dissolving a mixture of a 9-substituted purine nucleoside and a 7-substituted purine nucleoside in water, an alcohol such as methanol, ethanol, or the like, or a mixture solvent of water and an alcohol, while heating at between 50° C. and the reflux temperature, concentrating the solution

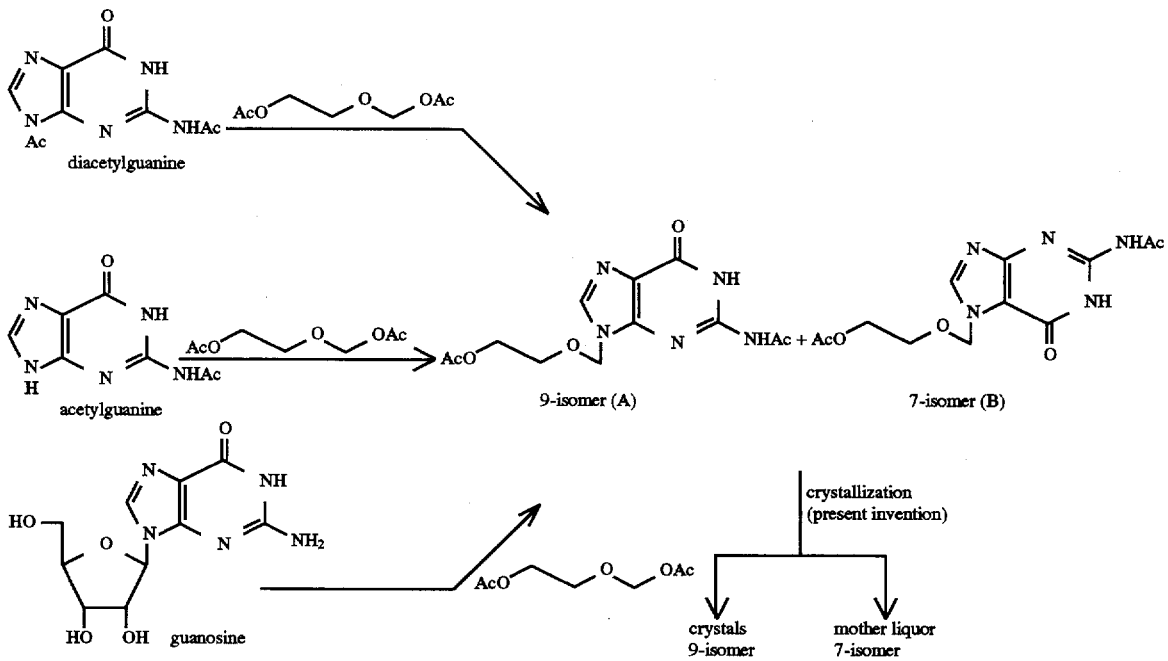

Synthesis of diacetylacyclovir from guanine derivatives

The 9-substituted purine nucleoside (diacetylacyclovir, Formula A in the scheme) is an important intermediate for acyclovir. However, in previously known synthetic methods, the by-production of the isomeric 7-substituted purine nucleoside (Formula B in the scheme) completely cannot be avoided. The desired 9-isomer can, however, be easily separated from a mixture of the 9- and 7-isomers by the separation method of the present invention.

The method of separation according to the present invention comprises crystallizing the 9-isomer selectively in a specific manner from a solution or suspension containing both a 9-substituted purine nucleoside represented by the if necessary, and cooling it to 0°–30° C. in order to crystallize the 9-substituted purine nucleoside. Here, crystals of the 9-substituted purine nucleoside may be added in a small amount as seed crystals.

A mixture of a 9-substituted purine nucleoside and a 7-substituted purine nucleoside to be treated according to the cooling crystallization may be one which has been isolated once from the reaction mixture, or may be the reaction mixture per se or a concentrate thereof, if necessary.

The method of crystallization with the use of a crystallizing solvent is effected by adding a solvent such as water, an alcohol such as methanol, ethanol, or the like, an organic acid ester such as ethyl acetate, or the like, a hydrocarbon such as toluene, xylene, or the like, a ketone such as acetone, methyl ethyl ketone, and the like, a halogenated hydrocarbon such as chloroform, dichloromethane, or the like, an ether such as diethyl ether, tetrahydrofuran, or the like, a nitrile such as acetonitrile, or the like, or a mixture thereof, as a crystallizing solvent to a solution or suspension containing a 9-substituted purine nucleoside and a 7-substituted purine nucleoside. A preferred crystallizing solvent for use is water, an alcohol such as methanol, ethanol, or the like, an organic acid ester such as ethyl acetate, or the like, a nitrile such as acetonitrile, or the like, or a mixture thereof.

The above mentioned solution or suspension containing a 9-substituted purine nucleoside and a 7-substituted purine nucleoside may be a reaction mixture per se or a concentrate thereof. In the case of a suspension, it is preferable to add a crystallizing solvent while heating, and then cool the solution thereafter. If the synthesis is conducted according to the method as described above, the reaction mixture is usually a high temperature suspension of a 9-substituted purine nucleoside containing a small amount of a 7-substituted purine nucleoside, and therefore the crystallization may be easily effected only by adding a crystallizing solvent directly to the reaction mixture.

The amount of a crystallizing solvent to be added varies depending upon the combination of a solvent which is used with a solution or suspension, but selection thereof is usually made in the range of a volumetric ratio of 0.5 to 50-fold on the basis of the solution or suspension.

The 9-substituted purine nucleoside crystals precipitated by crystallization may then be readily isolated, e.g., by filtration.

The separation method of the present invention may also be successfully carried out by resorting concurrently to such cooling crystallization and such crystallization with the use of a crystallizing solvent, both crystallizations having be explained just above.

EXAMPLES

Example 1

Synthesis of 9-((2-acetoxyethoxy)methyl)-$N^2$-acetyl guanine and 7-((2-acetoxyethoxy)methyl)-$N^2$-acetyl guanine from guanosine (1 of 2).

To 10 g of guanosine, 13 g of 2-oxa-1,4-butanediol diacetate (2 eq.), 36 g of acetic anhydride (10 eq.), 100 ml of dimethylformamide and 0.67 g (2.5 mol %) of p-toluenesulfonic acid monohydrate were added, and the mixture was stirred at 100° C. for 18 hours.

It was confirmed by comparison with authentic samples using high performance liquid chromatography that 9-((2-acetoxyethoxy)methyl)-$N^2$-acetylguanine and 7-((2-acetoxyethoxy)methyl)$N^2$-acetylguanine had been formed in 48% and 19% yields based on the guanosine, respectively, namely, at a ratio of 2.5:1.

Example 2

Synthesis of 9-((2-acetoxyethoxy)methyl)-$N^2$-acetylguanine and 7-((2-acetoxyethoxy)methyl) -$N^2$-acetylguanine from guanosine (2 of 2).

To 10 g of guanosine, 5.2 g of 1,3-dioxolane (2 eq.), 36 g of acetic anhydride (10 eq.), 100 ml of dimethylformamide and 0.67 g (2.5 mol %) of p-toluenesulfonic acid monohydrate were added, and the mixture was stirred at 100° C. for 18 hours.

2-oxa-1,4-butanediol diacetate was in situ formed in the reaction system and, via the same reaction as in Example 1, it was confirmed that 9-((2-acetoxyethoxy)methyl)-$N^2$-acetylguanine and 7-((2 -acetoxyethoxy)methyl)-$N^2$-acetylguanine had been formed in 46% and 18% yields based on the guanosine, respectively, by comparison with authentic samples using high performance liquid chromatography.

Example 3

Isomerization of 7-((2-acetoxyethoxy)methyl)-$N^2$-acetylguanine into 9-((acetoxyethoxy)methyl)-$N^2$-acetylguanine.

The reaction mixture obtained in Example 1 was directly subjected to distillation under a reduced pressure of 5 mmHg to remove the solvent, and the syrup residue was stirred at 100° C. for 18 hours, whereby 9-((2-acetoxyethoxy)methyl) -$N^2$-acetylguanine and 7-((2-acetoxyethoxy)methyl)-$N^2$-acetyl-guanine were obtained at a resulting ratio of 8.4:1.

The resulting reaction mixture was subjected to purification using column chromatography with 100 g of silica gel, whereby 6.7 g of 9-((2-acetoxyethoxy)methyl)-$N^2$-acetylguanine was obtained. Yield, 61%.

$^1$H NMR (300 MHz, DMSO-$d_6$) analytical values: δ, 1.95 (3H, s, Ac), 2.17 (3H, s, Ac), 3.63–3.73 (2H, m, H-3'), 4.05–4.11 (2H, m, H-4'), 5.48 (2H, s, H-1'), 8.13 (1H, s, H-8), 11.79 (1H, s, NH), 12.07 (1H, s, NH).

Mass spectral analytical value: MH$^+$=310.

Example 2

Synthesis of acyclovir from 9-((2-acetoxyethoxy)methyl)-$N^2$-acetylguanine.

To 5.0 g of 9-((2-acetoxyethoxy)methyl)-$N^2$-acetylguanine was added 50 ml of an aqueous 5% sodium hydroxide solution, and the mixture was sitrred for 24 hours at room temperature for reaction.

The resulting reaction solution was neutralized with 1N hydrochloric acid, and the precipitated crystals were collected by filtration, whereby 3.2 g of acyclovir was obtained. Yield, 92%.

$^1$ NMR (300 MHz, DMSO-$d_6$) analytical values: δ, 3.47 (4H, brs, H-3' & 4'), 4.66 (1H, brs, OH), 5.35 (2H, s, H-1'), 6.49 (2H, brs, NH$_2$), 7.81 (1H, s, H-8), 10.65 (1H, brs, NH).

Mass spectral analytical value: MH$^+$=226.

Example 5

Synthesis of 9-((1,3-diacetoxy-2-propoxy)methyl)-$N^2$-acetylguanine from guanosine.

To 10 g of guanosine, 17.5 g of 1,4-diacetoxy-3-acetoxymethyl-2-oxa-butane (2 equivalent), 36 g of acetic anhydride (10 equivalent), 100 ml of dimethylformamide and 0.67 g (2.5 mol %) of p-toluenesulfonic acid monohydrate were added, and the mixture was stirred at 100° C. for 18 hours for reaction. Subsequently, the solvent was distilled off under a reduced pressure of 5 mmHg, and the syrup residue was stirred at 100° C. for 18 hours.

Subsequently, the syrup was subjected to column chromatography using 300 g of silica gel and purified by eluting with a 7:1 mixed solvent of chloroform and methanol, whereby 6.9 g of 9-((1,3-diacetoxy-2-propoxy) methyl)-$N^2$-acetylguanine was obtained. Yield, 51%.

$^1$H NMR (300 MHz, CDCl$_3$) analytical values: δ, 12.20 (1H, br, NH), 10.4–10.6 (1H, br, NH), 7.78 (1H, s, H-8), 5.51 (2H, s, H-1'), 4.50–4.06 (4H, m, H-4', H-5'), 2.62 (3H, s, NHAc), 2.03 (6H, s, OAc×2).

Mass spectral analytical value: MH$^+$=382.

Example 6

Synthesis of ganciclovir from 9-((1,3-diacetoxy-2-propoxy)methyl)-$N^2$-acetylguanine.

To 5.0 g of 9-((1,3-diacetoxy-2-propoxy)methyl)-$N^2$-acetylguanine was added 50 ml of an aqueous 5% sodium hydroxide solution, and the mixture was stirred for 24 hours at room temperature for reaction.

The resulting reaction solution was neutralized with 1N hydrochloric acid, and the precipitated crystals were collected by filtration, whereby 3.0 g of gunciclovir was obtained. Yield, 90%.

$^1$H NMR (300 MHz, DMSO-$d_6$) analytical values: δ, 10.61 (1H, brs, NH), 7.80 (1H, s, H-8), 6.48 (2H, brs, NH$_2$), 5.44 (2H, s, H1'), 4.62 (2H, t, J=5.5 Hz, OH×2), 3.58–3.42 (5H, m, H-3', H-4' and H-5).

Mass spectrum analytical value: MNa$^+$=278.

Example 7

Synthesis of 9-((2-hydroxyethoxy)methyl)-adenine (in the formula (I), $R^1$=CH$_2$,$R^2$=(CH$_2$)$_2$, X=O, and Y=OH) from adenosine.

To 10 g of adenosine, 12 g of 2-oxa-1,4-butanediol diacetate (2 eq.), 34 g of acetic anhydride (10 eq.), 100 ml of acetonitrile and 0.63 g (2.5 mol %) of p-toluenesulfonic acid monohydrate were added, and the mixture was refluxed with stirring at an elevated temperature for 48 hours for reaction. Then, the solvent was removed by distillation under reduced pressure from the reaction mixture, and the residue was subjected to hydrolysis with aq. NaOH.

After neutralization, purification using the synthetic adsorption resin "SP-207" was carried out, whereby 5.4 g of the desired product was obtained. Yield, 69%.

$^1$H NMR (300 MHz, DMSO-$d_6$) analytical values: δ, 3.46 (4H, s, H-3' & 4'), 4.50 (1H, brs, OH), 5.25 (2H, s, H-1'), 7.00 (2H, s, NH$_2$), 8.17 (1H, s, H-2), 8.20 (2H, s, H-8).

Mass spectral analytical value: MH$^+$=210.

Example 8

Synthesis of 9-((2-hydroxyethoxy)methyl)-hypoxanthine (in the formula (I), $R^1$=CH$_2$, $R^2$=(CH$_2$)$_2$, X=O, and Y=OH) from inosine.

To 10 g of inosine, 12 g of 2-oxa-1,4-butanediol diacetate (2 eq.), 34 g of acetic anhydride (10 eq.), 100 ml of acetonitrile and 0.63 g (2.5 mol %) of p-toluenesulfonic acid monohydrate were added, and the mixture was refluxed with stirring at an elevated temperature for 48 hours for reaction. Then, the solvent was removed by distillation under reduced pressure from the reaction mixture, and the residue was subjected to hydrolysis with aq. NaOH.

After neutralization, purification using the synthetic adsorption resin "SP-207" was carried out, whereby 3.7 g of the desired product was obtained. Yield, 47%.

$^1$H NMR (300 MHz, DMSO-$d_6$) analytical values: δ, 3.44 (4H, s, H-3' & 4'), 4.30 (1H, brs, OH), 5.27 (2H, s, H-1'), 8.05 (1H, s, H-2), 8.31 (2H, s, H-8).

Mass spectrum analytical value: MH$^+$=211.

Example 9

Synthesis of 9-((2-acetoxyethoxy)methyl)-$N^2$-acetylguanine and 7-((2-acetoxyethoxy)methyl)-$N^2$-acetylguanine from guanosine.

To a mixture of 252.26 g of acetic anhydride and 52.36 g of 1,3-dioxolane was added 6.70 g of p-toluenesulfonic acid monohydrate. The mixture was stirred for 1 hour, added with 100 g of guanosine, and stirred at 100° C. for further 24 hours.

It was confirmed that 9-((2-acetoxyethoxy)methyl)-$N^2$-acetylguanine and 7-((2-acetoxyethoxy)methyl)-$N^2$-acetylguanine had been formed in 46% and 31% yields, respectively, by comparison with authentic samples using high performance liquid chromatography.

Example 10

Separation of 9-[(2-acetoxyethoxy)methyl]-$N^2$-acetylguanine by using a crystallizing solvent.

To 10 g of guanosine were added 13 g (2 equivalents) of 2-oxa-1,4-butanediol diacetate, 36 g (10 equivalents) of acetic anhydride, 100 ml of dimethylformamide and 0.67 g (2.5% by mol) of p-toluenesulfonic acid monohydrate, and the reaction was conducted by stirring the resulting mixture at 100° C. for 18 hours. The solvent was removed from the reaction mixture at a reduced pressure of 5 mmHg, and the remaining syrup-like substance was stirred at 100° C. for 18 hours to obtain a synthesis reaction solution containing 9-[(2-acetoxyethoxy)methyl]-$N^2$-acetylguanine and 7-[(2-acetoxyethoxy)methyl]-$N^2$-acetylguanine at a molar ratio of 79.3:8.6.

To 20 g portions of the synthesis reaction solution thus obtained were added in an 80 ml amount, the 6 different crystallizing solvents respectively, while stirring for crystallization. The crystals precipitated by stirring at room temperature (15°–25° C.) for another 1 hour were filtered and dried under reduced pressure.

The amount of each of the isomers contained therein was analyzed by high performance liquid chromatography (HPLC). The results are shown in Table 1. With the use of water, methanol, a water/methanol mixture solvent, ethyl acetate and ethanol as the crystallizing solvent, it was possible to obtain highly pure 9-isomer crystals while eliminating the 7-isomer.

TABLE 1

Crystallization of diacetylacyclovir from the reaction solution

| Reaction solution | Crystallizing solvent | Recovery yield(%) | Purity (area %)* 9-isomer 79.3 | 7-isomer 8.6 |
|---|---|---|---|---|
| 1 | MeOH/H$_2$O (1:1) | 65 | 97.0 | 0 |
| 2 | MeOH | 76 | 96.8 | 0.07 |
| 3 | H$_2$O | 78 | 96.9 | 0.07 |
| 4 | AcOEt | 86 | 92.9 | 1.7 |
| 5 | EtOH | 74 | 96.6 | 0.1 |
| 6 | Isopropyl alcohol | 32 | 94.3 | 1.7 |

*Area Ratio obtained by high performance liquid chromatography (HPLC)

Example 11

Separation of 9-[(2-acetoxyethoxy)methyl]-$N^2$-acetylguanine by cooling crystallization.

To 1 g of crude crystals of each of the 2 different kinds of 9-[(2-acetoxyethoxy)methyl]-$N^2$-acetylguanine (including the 7-isomer) was added an appropriate solvent from the 2 different ones while stirring, and dissolution was effected by heating at 50–°100° C., after which the solution was concentrated to about 10 ml. The concentrate was allowed to cool to room temperature (15–°25° C.) while stirring for cooling crystallization. The precipitated crystals were filtered and dried under reduced pressure.

The amount of each of the isomers was analyzed using high performance liquid chromatography (HPLC). The results are shown in Table 2. With the use of a water/ethanol mixture solvent as the crystallizing solvent, it was possible to obtain highly pure 9-isomer crystals while eliminating the 7-isomer.

TABLE 2

Cooling crystallization of purer diacetylacyclovir crystals

| Experiment No. | Crude crystals and Crystallizing solvent | Recovery yield(%) | Purity (area %)* 9-isomer | Purity (area %)* 7-isomer |
|---|---|---|---|---|
| 1 | Crude crystals (1) | 63 | 82.2 | 5.0 |
|   | Solvent (1): MeOH/H$_2$O (8:2) |  | 89.1 | 0.9 |
| 2 | Crude crystals (2) | 73 | 91.0 | 1.9 |
|   | Solvent (2): MeOH/H$_2$O (1:1) |  | 97.0 | 0 |

*Area ratio obtained by high performance liquid chromatography (HPLC)

Example 13

A mixture of 56.7 g (0.20 mol.) of guanosine, 102.1 g (1.0 mol.) of acetic anhydride and 1.2 g (0.01 mol.) of 85% phosphoric acid was heated at 100° C. for 80 minutes. To this reaction solution was added dropwise an acetic acid solution of 2-oxa-1,4-butanediol diacetate which had been prepared from 22.2 g (0.3 mol.) of 1,3-dioxolane, and the resulting solution was heated at 100° C. for further 18 hours. The reaction solution was concentrated under reduced pressure, and further heated for another 18 hours.

It was then cooled to 40° C., 170 ml of ethyl acetate was added thereto, and the mixture was cooled to room temperature. The crystals were filtered and dried under reduced pressure to obtain 45.8 g of 9-[(2-acetoxyethoxy)methyl]-N$^2$-acetylguanine in a yield of about 70%.

The isomer ratios observed for the reaction mixture prior to crystallization, the crystals and the crystallization mother liquor are shown in Table 3. Of the 9-isomer, 97.6% was recovered as crystals, while 92.8% of the 7-isomer remained in the mother liquor, clearly showing that the 9-isomer had been very efficiently separated.

TABLE 3

Isomer ratios

| | Isomer ratio (area %)* | | Recovery (%) | |
|---|---|---|---|---|
| | 9-isomer | 7-isomer | 9-isomer | 7-isomer |
| Reaction mixture | 86.2 | 4.5 | | |
| Crystals | 95.6 | 0.14 | 97.6 | 7.2 |
| Crystallization mother liquor | 36.0 | 26.8 | 2.4 | 92.8 |

*Area ratio obtained by high performance liquid chromatography (HPLC)

It is evident from the foregoing that it has become possible according to the present invention, to separate a 9-substituted purine nucleoside, which are important intermediates for acyclovir, ganciclovir, and the like by an industrially simple procedure. In other words, 9-substituted purine nucleosides which are important intermediates for the synthesis of acyclic nucleosides such as acyclovir, ganciclovir, and the like may be separated in an industrially simple manner and in a high yield, without the use of complicated methods of purification such as column chromatography.

What is claimed is:

1. A process for producing an acyclic nucleoside derivative represented by the formula (I):

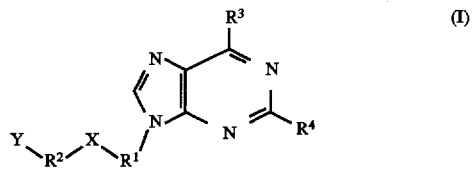

wherein R$^1$ represents a methylene group,

R$^2$ represents an alkylene group with 1 to 4 carbon atoms which may be substituted with hydroxyl group(s), amino group(s), alkoxyl group(s) with 1 to 12 carbon atoms, alkoxycarbonyl group(s), phosphono group(s), dialkoxyphosphoryl group(s), acyloxyl group(s) with 1 to 12 carbon atoms, acylamino group(s) with 1 to 12 carbon atoms, halogen atom(s) and/or silyloxyl group (s) represented by the formula (Ib):

wherein R$^5$, R$^6$ and R$^7$ which may be identical with, or different from, one another represent an alkyl group with 1 to 4 carbon atoms, a phenyl group or a benzyl group, R$^3$ and R$^4$ each represent independently a hydrogen atom, a halogen atom, a hydroxyl group, an amino group or a mercapto group, said hydroxyl group, amino group and mercapto group being one which may be substituted with an alkyl group with 1 to 12 carbon atoms, an acyl group with 1 to 12 carbon atoms or a silyl group represented by the formula (Ia):

wherein R$^5$, R$^6$ and R$^7$ are the same as those in the formula (Ib),

X represents an oxygen atoms, a sulfur atom, or an amino group, and

Y represents a hydroxyl group, an amino group, an alkoxyl group with 1 to 12 carbon atoms, a phosphono group, a dialkoxyphosphoryl group, an alkoxycarbonyl group with 1 to 12 carbon atoms, an acylamino group with 1 to 12 carbon atoms, a halogen atom, or a silyoxyl group represented by the above-mentioned formula (Ib), wherein acyl is a hydrocarbon carboxylic acid acyl having 1 to 12 carbons, and wherein said process comprises:

(1) heating a solution or suspension containing a 9-substituted purine nucleoside represented by the formula (I) and a 7-substituted purine nucleoside represented by the formula (II) at a temperature within the range from 50° C. to the reflux temperature:

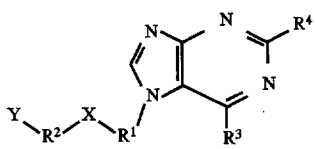 (II)

where $R^1$, $R^2$, $R^3$, $R^4$, X and Y are respectively the same as in the above-mentioned formula (I), and (2) crystallizing selectively the 9-substituted purine nucleoside from said solution or suspension.

2. The process of claim 1, wherein said 7-substituted purine nucleoside is 7-((2-acetoxyethoxy)methyl)-$N^2$-acetylguanine.

3. The process of claim 1, wherein said 7-substituted purine nucleoside is 7-((1,3-diacetoxy-2-propoxy)methyl)-$N^2$-acetylguanine.

4. The process of claim 1, wherein said 9-substituted purine nucleoside is 9-[(2-acetoxyethoxy)methyl]-$N^2$-acetylguanine, and said 7-substituted purine nucleoside is 7-[(2-acetoxyethoxy)methyl]-$N^2$-acetylguanine.

5. The process of claim 1, wherein said crystallizing selectively is carried out by cooling.

6. The process of claim 1, wherein said crystallizing selectively is effected by adding one or more solvents selected from the group consisting of water, alcohols and organic acid esters.

* * * * *